US007110582B1

(12) United States Patent　　(10) Patent No.: US 7,110,582 B1
Hay　　(45) Date of Patent: Sep. 19, 2006

(54) METHOD FOR DETERMINING BINOCULAR BALANCE AND DISORDERS OF BINOCULARITY OF AN INDIVIDUAL OR CLINICAL GROUPS OF INDIVIDUALS

(76) Inventor: Sam H. Hay, 310 Clinton Ave. West, Huntsville, AL (US) 35805

( * ) Notice: Subject to any disclaimer, the term of this patent is extended or adjusted under 35 U.S.C. 154(b) by 732 days.

(21) Appl. No.: 10/037,732

(22) Filed: Nov. 9, 2001

(51) Int. Cl.
G06K 9/00　　(2006.01)
A61B 13/00　　(2006.01)

(52) U.S. Cl. ..................... 382/128; 600/558
(58) Field of Classification Search ............... 382/128, 382/324, 117, 151, 130–133; 600/558; 351/221, 351/209
See application file for complete search history.

(56) References Cited

U.S. PATENT DOCUMENTS

| | | | | |
|---|---|---|---|---|
| 5,355,895 A | * | 10/1994 | Hay | 600/558 |
| 5,632,282 A | * | 5/1997 | Hay et al. | 600/558 |
| 6,095,989 A | * | 8/2000 | Hay et al. | 600/558 |
| 6,325,765 B1 | * | 12/2001 | Hay et al. | 600/558 |
| 6,419,638 B1 | * | 7/2002 | Hay et al. | 600/558 |
| 6,718,050 B1 | * | 4/2004 | Yamamoto | 382/117 |
| 6,916,096 B1 | * | 7/2005 | Eberl et al. | 351/209 |
| 2002/0036750 A1 | * | 3/2002 | Eberl et al. | 351/207 |
| 2002/0181774 A1 | * | 12/2002 | Ishikura | 382/190 |
| 2003/0071969 A1 | * | 4/2003 | Levine et al. | 351/221 |
| 2004/0165099 A1 | * | 8/2004 | Stavely et al. | 348/345 |

* cited by examiner

*Primary Examiner*—Duy M. Dang
(74) *Attorney, Agent, or Firm*—Mark Clodfelter

(57) ABSTRACT

A method for identifying particular disorders of the eyes is disclosed. Initially, an image of the eyes in digital format is taken by a reflex photometer and the image provided to a computer programmed to run a plurality of algorithms that are associated with each type of disorder. Results of the algorithms are plotted in a format so that any of the eye disorders associated with the algorithms are readily apparent.

14 Claims, 7 Drawing Sheets

Amblyopic Factors

Alignment Factors

Balance: left/right ratio

Refractive Factors

HIRSCHBERG NASAL DEVIATION

METHOD FOR DETERMINING BINOCULAR BALANCE AND DISORDERS OF BINOCULARITY OF AN INDIVIDUAL OR CLINICAL GROUPS OF INDIVIDUALS

FIELD OF THE INVENTION

This invention relates to a method of assessment of binocular balance, binocularity, and of certain monocular parameters of paired eyes of an individual, and particularly to such a method wherein a plurality of statistical parameters are evaluated to determine, to a high probability, whether an individual is affected by Amblyopia, Strabismus, Reading Difficulties or other problems relating to binocular balance. As a corollary, a method of determining a plurality of standard statistical measurements such as the mean, median, standard deviation, confidence interval and other like statistical determinations of value parameters of the Wavefront images of groups of persons with similar and dissimilar disease states is disclosed. This technique permits the generic generalization and mathematical description of image characteristics of diverse disease and ocular states in such groups of persons.

BACKGROUND OF THE INVENTION

Normal binocular visual perception requires a degree high degree of similarity in the presentation of images formed by the right and left eyes and presented to the visual centers of the brain to generate a single visual perception. In order to compare the similarity of optical quality and other ocular characteristics of the right and left eyes with the technique of the present invention, It is a necessity to predetermine certain ocular and optical characteristics of a monocular state of each of the eyes. Such determinations include (1) the individual alignment of the right and left eye to a fixation target, (2) the individual ocular refractive status of the right and left eye and (3) other elements contained in the wavefront that are found to correlate with or predispose to, ocular-optical impediments to successful visual integration of the right and left visual image to produce normal single vision. Such impediments result in or are associated with Amblyopia, Strabismus, Binocular Balance and some reading difficulties.

Amblyopia is a neurological disease resulting in Central Nervous System (brain) neuro-pathologic changes that are related either as a cause or result of some underlying abnormality in the monocular and binocular state. Most modern thought is that individual difference between the two eyes, either in alignment or refractive power or a combination of the two, results in an inability of the two eyes to generate individual right and left images that can be converted into a single mental perception by the brain's visual centers. In the case of misalignment, the eyes are pointing in different directions and the images generated by the eyes cannot be blended together into a single perception. In the case of anisometropia (optical refractive powers of the eyes being different), the images are of different optical size, with one eye more out of focus as compared to the other eye. As a result, the differently-sized images cannot be fused into a single visual image. Frequently, both of these situations are found in Amblyopia. Determining abnormalities in the right and left eye and binocular relationships that result in dissimilarity of image formation frequently predict presence of the amblyopic condition. Another aspect that is less appreciated is that an abnormal neural state affects changes in the eyes by some type of reverse bio-feedback mechanism going from the brain to the eyes. This abnormal neural-feedback to the eyes could result in an abnormality of development or innervation of the extra-ocular muscles. Neurologic innervation, neural disease processes such as optic neuritis occurring during times of visual development, can account for developmental abnormalities of ocular development and or optical configuration of the eyes, all or part of which may result in some of those extreme ocular abnormalities associated with an amblyopic condition.

Evaluation of binocularity of a subject by a trained clinician is generally a subjective process. In the simplest format, such an evaluation is made simply by observing whether both pupils of a subject are centered in the eye fissure, i.e. there is an equal amount of white on both sides of the iris of both eyes while the subject is gazing at a fixed point. In addition, there are several other methods of determining more precisely the presence of binocular cooperation, or integration of the images into a single mental visual perception. Some of these methods include the "Cover/Cover/Uncover" Test of fixation and alignment, or the Stereoscopic Vision and certain Electro-physiologic measurements of visual response found in brain waves in response to a visual stimulus. However, such evaluations are generally dependent on cooperation of the subject and skill of the clinician. For instance, getting a pre-verbal child to gaze at a fixed point to determine individual fixation may be a problem in itself.

A number of devices have been constructed to optically evaluate Wavefront aberrations. In these devices, monocular refractive characteristics of optical power are used to identify and extract location, degree and kind of optical degradation existing within the pupillary aperture. Such knowledge permits precise remedial corneal contouring in order to correct the refractive error. However, these devices do nothing with respect to identification of problems related to visual integration of separate images from the right and left eye into a single mental perception.

Applicants method additionally permits a mathematical description that when plotted, results in a visual "profile" of a disease process found in broad groups of persons suffering with similar ocular states or diseases. This is accomplished by mathematically summing the individual algorithmic parameters of a particular person with those corresponding parameters of other like persons with similar diseases. Once accomplished and entered into a spread sheet, any or all of a number of statistical techniques may be utilized to generate statements concerning these group parameters of disease or inherent optical-ocular condition. In this manner, any ocular Wavefront image of an individual may be expressed statistically as possessing some degree of probability of being contained in some known and statistically defined disease grouping. All eye conditions and diseases, such as Amblyopia, Strabismus, Refraction, Cataracts and Retinal diseases, along with certain medical conditions that present an ophthalmic manifestation such as diabetes, hypertension, brain tumor and others may be approached in like fashion.

It is one object of this invention to extract a plurality of statistical relationships from a digital image of eyes of a subject, and to determine binocular status of the eyes from these relationships. It is another object of this invention to present such statistical relationships in a manner to allow a clinician to identify eye problems associated with binocularity. Other objects will become clear upon a reading of the following specification.

SUMMARY

A method for ascertaining whether an individual has certain eye disorders relating to binocularity, or monocular impediments to binocularity or the antecedents of Amblyopia, reading disorders, or the ocular effects of Amblyopia or Strabismus is disclosed. In this method, the eyes of the subject are imaged by a reflex photometer, which captures images of the eye's Retinal Reflex Wavefront in a digital format. The image of the retinal reflex is obtained, and a number of statistical algorithms performed thereupon by a computer to determine a plurality of parameters from each of the retinal reflexes. These parameters in turn are plotted in a format so that any disorders that may be present are clearly evident.

BRIEF DESCRIPTION OF THE DRAWINGS

FIG. 6 is a graphical presentation of a non-normal eye contrasting how median results of bilateral balance ratio analysis thereof differs from the statistically normal eye as shown in FIG. 1a.

DETAILED DESCRIPTION OF THE DRAWINGS

Figure 1B:
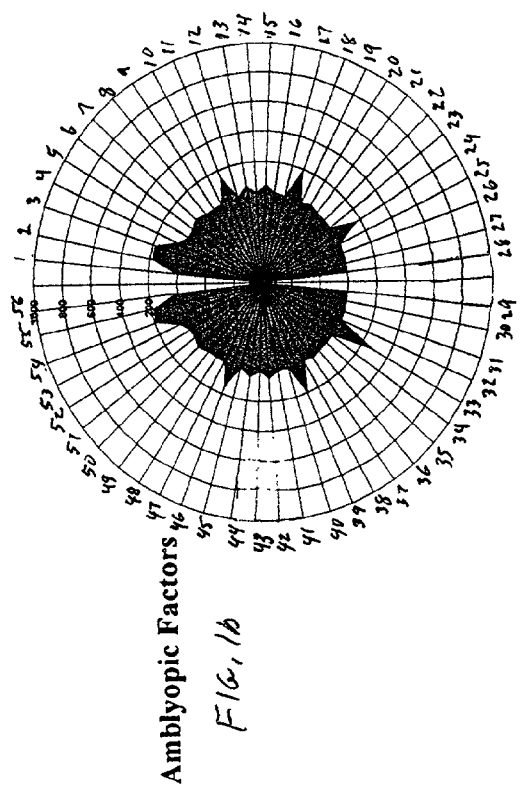
FIG. 1b illustrates median values of a control group of individuals having relatively normal eyes, in plot form, of amblyopic factors.

Applicant's invention presents a standardized afferent visual stimulus to an individual, who makes an efferent sensory/motor response to that stimulus in an effort to optimize the visual experience. Since characteristics of image acquisition, camera, flash and stimulus presentation, subject task assignment and all other circumstances of imaging are the same for all subjects, the resultant image is an optical manifestation of a person's eyes in a state of "Optimal Visual Perception" (OVP). In such a circumstance, one individual's image may be compared to a subsequent image or to other person's images as previously described. The image of the binocular wavefront from both eyes of an individual may be considered a unique, non-invasive signature of the particular binocular relationship of the eyes of that person.

The binocular wavefront from both eyes may include many wavefront variations between the eyes, and further contain variations between individuals whose eyes and visual systems may be considered normal. As such, the wavefront configuration is an optical composite of the optical effects of ocular anatomy, optical power of the eyes, media characteristics, degree of accommodation and sensory/motor component of ocular alignment. While the nature and meaning of some of the patterns and variations of the binocular wavefront are not known, some patterns are significant as to their clinical meaning. Here, Applicant has identified many of these image features by algorithm, and utilizes the algorithms to graphically profile the integrated wavefront from both eyes in a state of "Optimal Visual Perception" to determine whether optical or neurological diseases relating at least to binocularity, alignment and refraction are present.

Digital capture of images of eyes of a subject may be done by a retinal reflex capturing device as disclosed in Applicant's U.S. Pat. No. 6,095,989, issued Aug. 1, 2000, and which is incorporated herein by reference. In this device, a CCD array of 765 by 510 pixels captures an image containing both eyes of a subject with approximately 64,000 possible intensity levels for each pixel. Image data is recorded in a digitized format and exported directly into Microsoft Access (TM), where the data is archived. Images collected in such a manner appear as a black and white photograph, and are of little clinical value due to the fact that much of the diagnostic information contained in the wave front is concealed in the blur of the relatively bright retinal reflex. Pseudo-color image analysis and enhancement techniques allow visualization of patterns within the Wavefronts. Certain of these patterns strongly correlate with alignment, astigmatism, optical media and refraction, and may be considered signatures of these ocular states. Likewise, there are characteristic signature features related to binocularity in both amblyopic and non-amblyopic subjects.

Applicant's invention determines light intensity levels in the wavefront of the reflex of a subject's right and left pupils, on a pixel by pixel basis. Subsequently, a plurality of algorithms mathematically compares intensity values of pixels imaging one eye reflex with intensity values of pixels imaging the other eye reflex. In some algorithms, the area around the reflex of the eyes may be examined, such as the iris region and visible portion of the sclera (whites of the eyes). A standard image of a spherical ruby lens is generated with each image as a reference value for instrument alignment and flash intensity determinations. The resulting statistical values of these calculations and measurements are basically a plurality of numerical expressions mathematically representative of the pupillary reflexes of a particular person, or if combined as previously described, of a class of persons with a particular disease process.

As an example of this technique, the broad group category of "Normal Binocular Image" (images obtained form a group of persons having at 20/30 or better vision uncorrected and orthophoric (both eyes straight) has been defined for the detection of Amblyopia and other binocular disease states. This mathematical definition can be represented as either a mathematical statement as shown in table 1 or plotted graphically as shown in FIGS. 1a, 1b, 1c and 1d.

| NAME OF ALGORITHM BILATRL BAL. RATIO | MEDIAN NORMAL VALUES | DESIG. NUMBR |
|---|---|---|
| R/LPSpikePatchEdgeMedian | 1.00593449 | 1 |
| RP/LPSpikePatchEdgeStd | 1.25900165 | 2 |
| RP/LPMean | 1.01997038 | 3 |
| RP/LPMedian | 1.02935212 | 4 |
| RP/LPStd | 1.16714214 | 5 |
| RP/LPSkewness | 0.82377437 | 6 |
| RP/LPPeakedness | 0.83179395 | 7 |
| RP/LPRadMeanHarm | 1.00679255 | 8 |
| RP/LPMoment.N20 | 0.96590409 | 9 |
| RP/LPMoment.N21 | 0.9193478 | 10 |
| RP/LPMoment.Hu4 | 0.9970549 | 11 |
| RP/LPTopography.Rows.Linear.Intercept | 0.98696865 | 12 |
| RP/LPTopography.Rows.Linear.Slope | 0.99585671 | 13 |
| RP/LPTopography.Rows.Quad.Intercept | 0.81816553 | 14 |
| RP/LPTopography.Rows.Quad.Slope | 0.99855347 | 15 |
| RP/LPTopography.Rows.Quad.Quartic | 0.97012394 | 16 |
| RP/LPTopography.Cols.Linear.Intercept | 1.07950805 | 17 |
| RP/LPTopography.Cols.Linear.Slope | −0.11944885 | 18 |
| RP/LPTopography.Cols.Quad.Intercept | 0.92946604 | 19 |
| RP/LPTopography.Cols.Quad.Slope | 1.17619174 | 20 |
| RP/LPTopography.Cols.Quad.Quartic | 1.22233382 | 21 |
| RP/LPHirschberg.RadiusMM | 0.83654738 | 22 |
| RP/LPHirschberg.TotalDeviationAxis | 1.25903333 | 23 |
| RP/LPHirschberg.TotalDeviation | 0.83653999 | 24 |
| RP/LPHirschberg.NasalDeviation | 0.7142727 | 25 |
| RP/LPHirschberg.VerticalDeviation | 1 | 26 |
| RP/LPIntraSymmetry | 0.9961078 | 27 |

AMBLYOPIC FACTORS >>>>>>>>>

| | | |
|---|---|---|
| LPSpikePatchEdgeStd | 13.22015 | 1 |
| LPMean | 179.10155 | 2 |
| LPMedian | 186.95475 | 3 |
| LPStd | 40.22095 | 4 |
| LPSkewness | −1.13885 | 5 |
| LPPeakedness | 4.09335 | 6 |
| LPRadMeanHarm | 31.4769 | 7 |
| LPMoment.N20 | 0.00040109 | 8 |
| LPMoment.N21 | 1.6179E-07 | 9 |
| LPMoment.Hu4 | −12.42115 | 10 |
| LPTopography.Rows.Linear.Intercept | 150.76845 | 11 |
| LPTopography.Rows.Linear.Slope | 0.332535 | 12 |
| LPTopography.Rows.Quad.Intercept | 50.12595 | 13 |
| LPTopography.Rows.Linear.Slope | 0.332535 | 14 |
| LPTopography.Rows.Quad.Intercept | 50.12595 | 15 |
| LPTopography.Rows.Quad.Slope | 3.93675 | 16 |
| LPTopography.Rows.Quad.Quartic | −0.027522 | 17 |
| LPTopography.Cols.Linear.Intercept | 180.0216 | 18 |
| LPTopography.Cols.Linear.Slope | 0.065252 | 19 |
| LPTopography.Cols.Quad.Intercept | 26.80885 | 20 |
| LPTopography.Cols.Quad.Slope | 5.1977 | 21 |
| LPTopography.Cols.Quad.Quartic | −0.0397975 | 22 |
| LPHirschberg.RadiusMM | 0.33245 | 23 |
| LPHirschberg.TotalDeviationAxis | 168.6901 | 24 |
| LPHirschberg.TotalDeviation | 3.657 | 25 |
| LPHirschberg.NasalDeviation | −3.1358 | 26 |
| LPHirschberg.VerticalDeviation | 0.62717 | 27 |
| LPIntraSymmetry | 0.93546 | 28 |
| RPIntraSymmetry | 0.940565 | 29 |
| RPHirschberg.VerticalDeviation | −0.62717 | 30 |
| RPHirschberg.NasalDeviation | −3.1358 | 31 |
| RPHirschberg.TotalDeviation | 3.1979 | 32 |
| RPHirschberg.TotalDeviationAxis | 279.72 | 33 |
| RPHirschberg.RadiusMM | 0.29072 | 34 |
| RPTopography.Cols.Quad.Quartic | −0.0473615 | 35 |
| RPTopography.Cols.Quad.Slope | 6.02155 | 36 |
| RPTopography.Cols.Quad.Intercept | 13.8925 | 37 |
| RPTopography.Cols.Linear.Slope | −0.012294 | 38 |
| RPTopography.Cols.Linear.Intercept | 209.5902 | 39 |
| RPTopography.Rows.Quad.Quartic | −0.0309945 | 40 |
| RPTopography.Rows.Quad.Slope | 4.5243 | 41 |
| RPTopography.Rows.Quad.Intercept | 45.1951 | 42 |
| RPTopography.Rows.Linear.Slope | 0.365655 | 43 |
| RPTopography.Rows.Quad.Intercept | 45.1951 | 44 |
| RPTopography.Rows.Linear.Slope | 0.365655 | 45 |
| RPTopography.Rows.Linear.Intercept | 160.0171 | 46 |
| RPMoment.Hu4 | −12.5746 | 47 |
| RPMoment.N21 | 1.5087E-07 | 48 |
| RPMoment.N20 | 0.00039074 | 49 |
| RPRadMeanHarm | 31.85425 | 50 |
| RPPeakedness | 3.38515 | 51 |
| RPSkewness | −0.979875 | 52 |
| RPStd | 47.52005 | 53 |
| RPMedian | 192.57675 | 54 |
| RPMean | 179.74495 | 55 |
| RPSpikePatchEdgeStd | 16.7209 | 56 |

REFRACTION>>>>>>>>>

| | | |
|---|---|---|
| LPTopography.Cols.Quad.Quartic | −0.0397975 | 1 |
| LPTopography.Cols.Quad.Slope | 5.1977 | 2 |
| LPTopography.Cols.Quad.Intercept | 26.80885 | 3 |
| LPTopography.Cols.Linear.Slope | 0.065252 | 4 |
| LPTopography.Cols.Linear.Intercept | 180.0216 | 5 |
| LPTopography.Rows.Quad.Quartic | −0.027522 | 6 |
| LPTopography.Rows.Quad.Slope | 3.93675 | 7 |
| LPTopography.Rows.Quad.Intercept | 50.12595 | 8 |
| LPTopography.Rows.Linear.Slope | 0.332535 | 9 |
| LPTopography.Rows.Linear.Intercept | 150.76845 | 10 |
| LPMoment.Hu4 | −12.42115 | 11 |
| LPMoment.N21 | 1.6179E-07 | 12 |
| RPMoment.N21 | 1.5087E-07 | 13 |
| RPMoment.Hu4 | −12.5746 | 14 |
| RPTopography.Rows.Linear.Intercept | 160.0171 | 15 |
| RPTopography.Rows.Linear.Slope | 0.365655 | 16 |
| RPTopography.Rows.Quad.Intercept | 45.1951 | 17 |
| RPTopography.Rows.Quad.Slope | 4.5243 | 18 |
| RPTopography.Rows.Quad.Quartic | −0.0309945 | 19 |
| RPTopography.Cols.Linear.Intercept | 209.5902 | 20 |
| RPTopography.Cols.Linear.Slope | −0.012294 | 21 |
| RPTopography.Cols.Quad.Intercept | 13.8925 | 22 |
| RPTopography.Cols.Quad.Slope | 6.02155 | 23 |
| RPTopography.Cols.Quad.Quartic | −0.0473615 | 24 |

ALIGNMENT >>>>>>>

| | | |
|---|---|---|
| LPStd | 40.22095 | |
| LPMedian | 186.95475 | 1 |
| LPMean | 179.10155 | 2 |
| LPSpikePatchEdgeStd | 13.22015 | 3 |
| LPHirschberg.RadiusMM | 0.33245 | 4 |
| LPHirschberg.TotalDeviationAxis | 168.6901 | 5 |
| LPHirschberg.TotalDeviation | 3.657 | 6 |
| LPHirschberg.NasalDeviation | −3.1358 | 7 |
| LPHirschberg.VerticalDeviation | 0.62717 | 8 |
| LPIntraSymmetry | 0.93546 | 9 |
| RPIntraSymmetry | 0.940565 | 10 |
| RPHirschberg.VerticalDeviation | −0.62717 | 11 |
| RPHirschberg.NasalDeviation | −3.1358 | 12 |
| RPHirschberg.TotalDeviation | 3.1979 | 13 |
| RPHirschberg.TotalDeviationAxis | 279.72 | 14 |
| RPHirschberg.RadiusMM | 0.29072 | 15 |
| RPSpikePatchEdgeStd | 16.7209 | 16 |
| RPMean | 179.74495 | 17 |
| RPMedian | 192.57675 | 18 |
| RPStd | 47.52005 | 19 |

A graphic presentation of the values of "Normal Binocular Image" (FIGS. 1a, 1b, 1c, 1d) is easiest to appreciate, and includes the above respective factors in graphic form. This presentation can be calculated as median or mean or with or without confidence intervals. The median of the Normal Group values of the above algorithms is presented in FIGS. 1a, 1b, 1c and 1d, which describe four binocular factors found to strongly correlate with the presence of Amblyopia. They are Balance Ratio (FIG. 1a), Amblyopic factors (FIG. 1b), Refractive Factors (FIG. 1c) and Alignment Factors (FIG. 1d). The description of "Normal" is the most important of all determination, since any individual whose image values are different is by definition abnormal. In the following examples of persons with various ocular disease states this determination is easily made by observation. It is just as easily made by computing the statistical evaluation of the distribution of the data and a probability that some unknown image either is or is not composed of a "normal" data distribution.

Figure 1D:
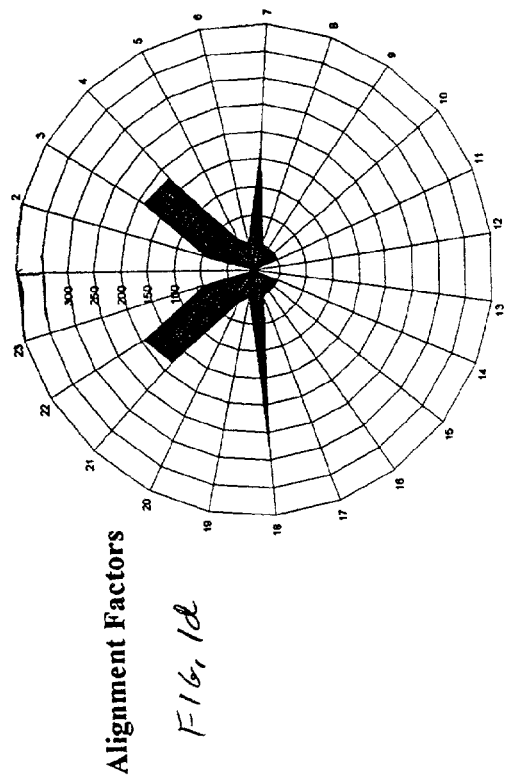
FIG. 1d illustrates median values of a control group of individuals having relatively normal eyes, in plot form, of alignment factors of the present invention.
Figure 1A:
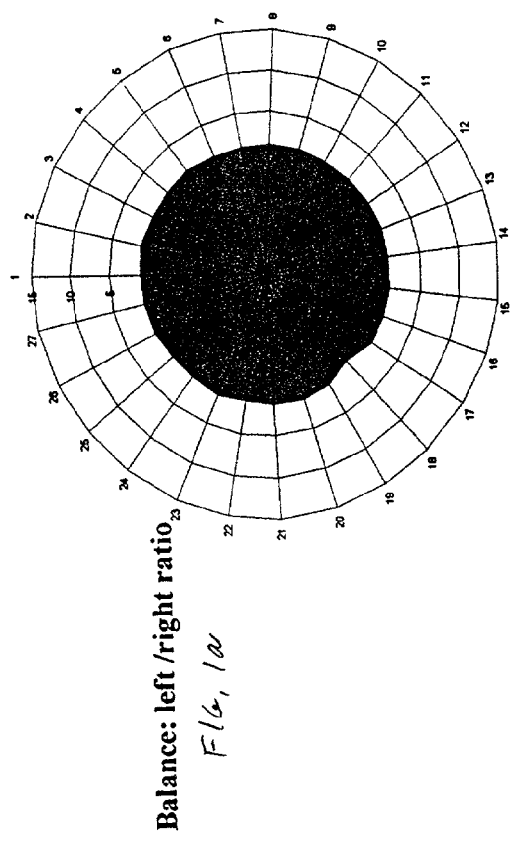
FIG. 1a illustrates median values of a control group of individuals having relatively normal eyes, in plot form, of a balance ratio.

Information contained in FIGS. 1a, 1b, 1c and 1d is read by starting at the Amblyopic Factors (FIG. 1b). This is a series of 27 values found in each eye and obtained from 27 of the Metrological Algorithms defined hereinafter and in Appendix A. From these values, the Balance (FIG. 1a) between the eyes can be ascertained by calculating a ratio relationship, left to right or vice versa. For normal eyes each of these values are expected to be close to unity since both eyes are of equal optical refractive power, equal optical-ocular configuration and alignment, and are seeing normally. The factors associated with Amblyopia are Refractive (FIG. 1c) and Alignment (FIG. 1d), and should be close to being mirror images of each other in normal eyes. Amblyopic, Alignment and Refractive Factors are similar to "butterfly" wings, with the right and left eyes represented by the right and left wings. Individuals with perfect eyes and binocular systems that present highly similar images to the brain for visual integration must always have symmetrical Wavefront reflexes as illustrated in FIGS. 1a–1d.

Direction of Gaze and Determination of Validity of Informational Content of Binocular Images It is important to determine informational quality and content of the image prior to analysis and inference of a clinical deduction. In particular, quality of fixation and centrality of the subject's gaze at the time of imaging is important since it is observed that poor fixation of both eyes results in a spurious analytical result and information as to optical and ocular status of that individual. At least one eye must be fixing on the target for validity of the analysis. Additionally, information as to the proper fixation status of at least one eye of a binocular image must be deduced to determine if a state of "Optimal Visual Perception" is present in that particular subject. This is necessary in order to compare and average eye values either with eye values of other groups of subjects or to effect comparisons between the eyes of the subject.

Vertical and Horizontal Deviation determinations are accomplished by utilization of the following algorithms, either singularly or in combination. A brief description of the algorithms are provided in Appendix A attached hereto.

Gaze Direction Algorithms

InterSymmetry

LPCenterCol

RPCenterCol

LiCenterCol

RICentercol

LPHirschberg.RadiusMM

RPHirschberg.RadiusMM

LPHirschberg.TotalDeviationAxis

RPHirschberg.TotalDeviationAxis

LPHirschberg.TotalDeviation

RPHirschberg.TotalDeviation

LPHirschberg.NasalDeviation

RPHirschberg.NasalDeviation

LPHirschberg.VerticalDeviation

RPHirschberg.VerticalDeviation

LPTopography.Rows.Linear.Intercept

RPTopography.Rows.Linear.Intercept

LPTopography.Rows.Quad.Intercept

RPTopography.Rows.Quad.Intercept

LPTopography.Rows.Quad.Slope

RPTopography.Rows.Quad.Slope

LPTopography.Rows.Quad.Quartic

RPTopography.Rows.Quad.Quartic

LPTopography.Cols.Linear.Intercept

RPTopography.Cols.Linear.Intercept

LPTopography.Cols.Linear.Slope

RPTopography.Cols.Linear.Slope

LPTopography.Cols.Quad.Intercept

RPTopography.Cols.Quad.Intercept

LPTopography.Cols.Quad.Slope

RPTopography.Cols.Quad.Slope

LPTopography.Cols.Quad.Quartic

RPTopography.Cols.Quad.Quartic

LPTopography.Rows.Linear.Slope

RPTopography.Rows.Linear.Slope

Figure 2:
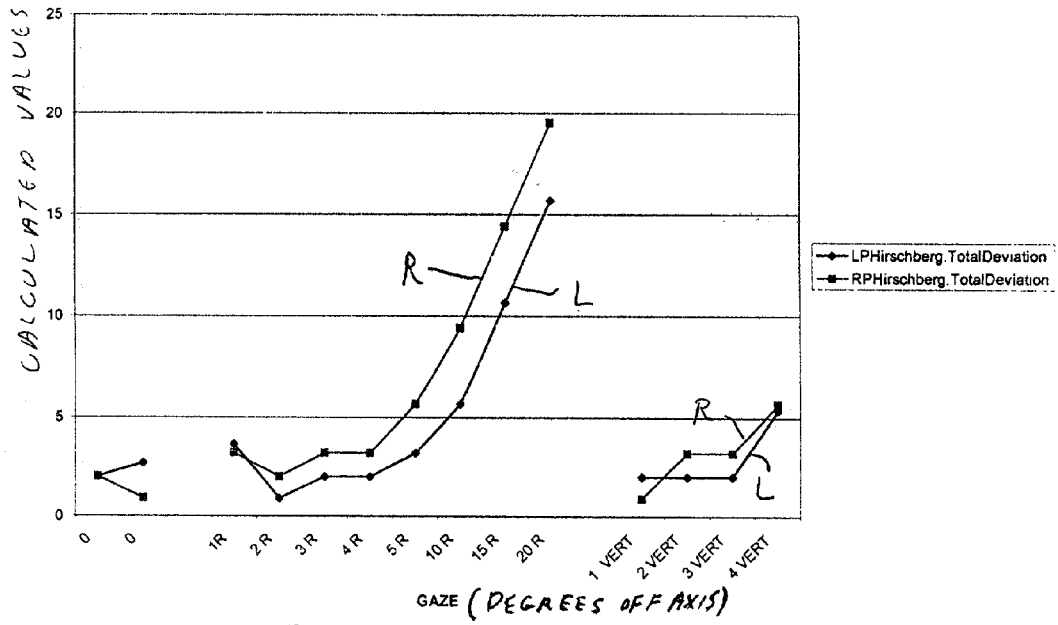
FIGS. 2, 3 and 4 illustrate graphs of algorithms for determining horizontal and vertical alignment in various degrees of off fixation from straight ahead gaze.

Plotting the above calculated values for the right an left eyes results in a method of determining fixation of at least one eye, or as a corollary, of neither eye fixating on the target, as can be seen in the graph of FIG. 2. In this example, the Hirschberg total deviation is calculated and plotted with both eyes in various degrees of right directed, horizontal deviation from central gaze. In this graph, degrees of deviation are plotted horizontally and calculated values of Hershberg total deviation are plotted along the vertical axis. As such, the right eye (R) becomes more "out-turning" and the left eye (L) becomes more "in-turning", while in fact both eyes are in proper alignment and pointing straight but just not at the intended target. This can easily be seen in FIG. 2 wherein the number of degrees of "Off Fixation" is indicated along the horizontal "X" axis. Of course the same algorithms and computation can be used for determinations of gaze left of fixation.

Still referring to FIG. 2, vertical "off fixation" is also plotted and is represented by the 4 values (for each eye) on the right side of the graph. Again, the number of degrees of vertical misalignment is calculated on the horizontal axis, with calculated values of Hershberg total deviation being plotted along the vertical axis. In this example, both eyes are elevated and off of central fixation and the resultant deviation is clearly seen.

Figure 3:
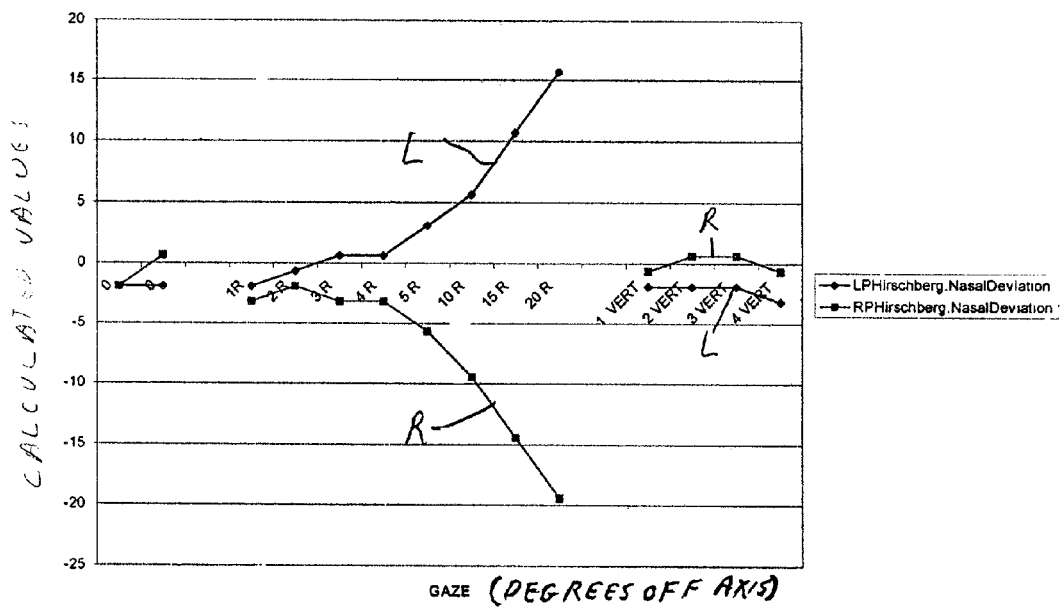
Figure 4:
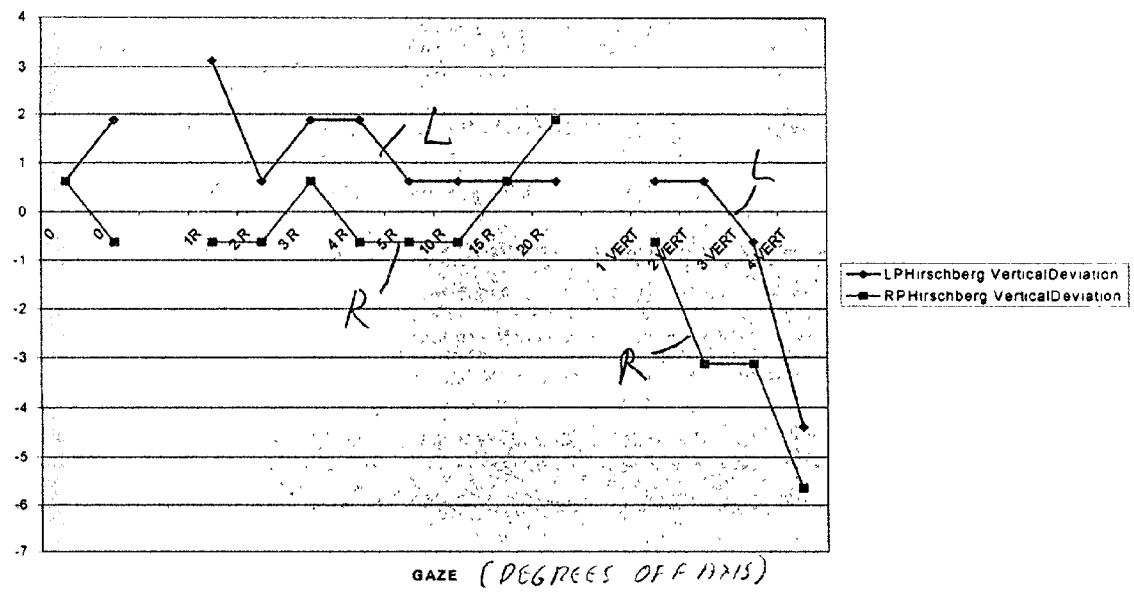

FIG. 3 shows Hershberg nasal deviation for the amount of deviation of the eyes shown in FIG. 2, i.e. the eyes progressively being directed horizontally to the right of a fixation target. As shown, values for the right eye R become increasingly negative with corresponding increasing degrees of right deviation, while values for the left eye become increasingly positive with corresponding increasing degrees of right deviation. While the Hershberg nasal deviation algorithm as graphed in FIG. 3 is clearly sensitive to horizontal deviation, it is not particularly sensitive to vertical deviation, as seen for the 4 values 1vert, 2vert, 3vert and 4vert plotted on the right side of FIG. 3. In this scale, 1vert is one degree from horizontal of vertical inclination, 2vert is two degrees of inclination from horizontal, and so forth. Thus, to determine vertical deviation, a Hershberg vertical deviation algorithm is used, and may be plotted as shown on the right side of FIG. 4. Here, it is seen that with increasing inclination of the eyes in degrees, as indicated by 1vert, 2vert, 3vert, and 4vert, meaning that the eyes are looking upward 1 degree from horizontal, 2 degrees from horizontal, and so forth, the calculated values for each of the eyes become increasingly negative. In addition, it is seen that this algorithm is particularly sensitive to vertical misalignment of the eyes from horizontal. When the eyes are moved horizontally, as indicated on the left side of FIG. 4, the results are not particularly useful.

Where an analysis is found to be valid as described above, by using these binocular computations and selected values from the other prior identified algorithmic values, determinations may be made as to whether a subject has an alignment disorder, such as a form of strabismus, a misaligned gaze fixation problem, or a refraction problem. In addition, other selected calculations are predictive of degree to which an individual is afflicted with a disorder. In general, in a pair of "normal" eyes, the ratio of values of the right pupil/left pupil approaches unity since both eyes are fixing on a target and are optically close to being equal. This is a result of bilateral, generally symmetrical propagation of the wavefront into and out of the eyes. Such generally symmetrical propagation of the wavefront is not found in wavefront images of persons with alignment, fixation and other disorders because the eyes are either not equally oriented to a common fixation point or not equal in refractive power. Additional statistical indications of imbalance and aberration may also be induced by abnormalities of ocular anatomy and/or optical effects of tangentially illuminating and imaging through a non-axial, strabismic eye. In any event, these algorithms are a manifestation of the totality of those ocular factors representative of that individual's binocular status and his response to a standardized stimulus. Selected ones of these algorithms permit a valid method of comparison with respect to changes of binocularity of an individual over time.

Signal processing algorithms are written in Matlab™ to detect and analyze the numerical values of the wavefront image data. For example, of 182 or so right and left monocular numeric relationships identified by this program, and which are included herein as appendix A, some have been identified as being predictive of alignment disorders, while others have been identified as being predictive of disorders relating to differing refractive powers of the eyes. It has been found that some of these algorithms are associated with a particular optical/ocular disorder more strongly than with other disorders. Additionally, one algorithm may be associated with more than one condition or ocular state. In some instances, the relationship between the clinical condition of the eye and the correlating algorithm is incompletely understood and no clinical interpretation of the correlation can be made other than the fact that the correlation between the clinical condition and the algorithm exists.

Algorithmically derived values of a Wavefront correlating with Anisometropia (dissimilarity of refractive power of the eyes) and/or misalignment (Stabismus) may be combined to detect Amblyopia. Yet other algorithms are indicative of a "bilateral balance" ratio between the eyes, which is obtained by dividing results of selected algorithms from the left eye by the results of the same algorithms from the right eye. This bilateral balance ratio has been found to correlate to both Amblyopia and Reading Disorders. In addition, the bilateral balance ratio may be indicative of an optically normal eye, so that if the subject still has a problem, other factors, such as neurological or psychological, may be explored.

Figure 5:
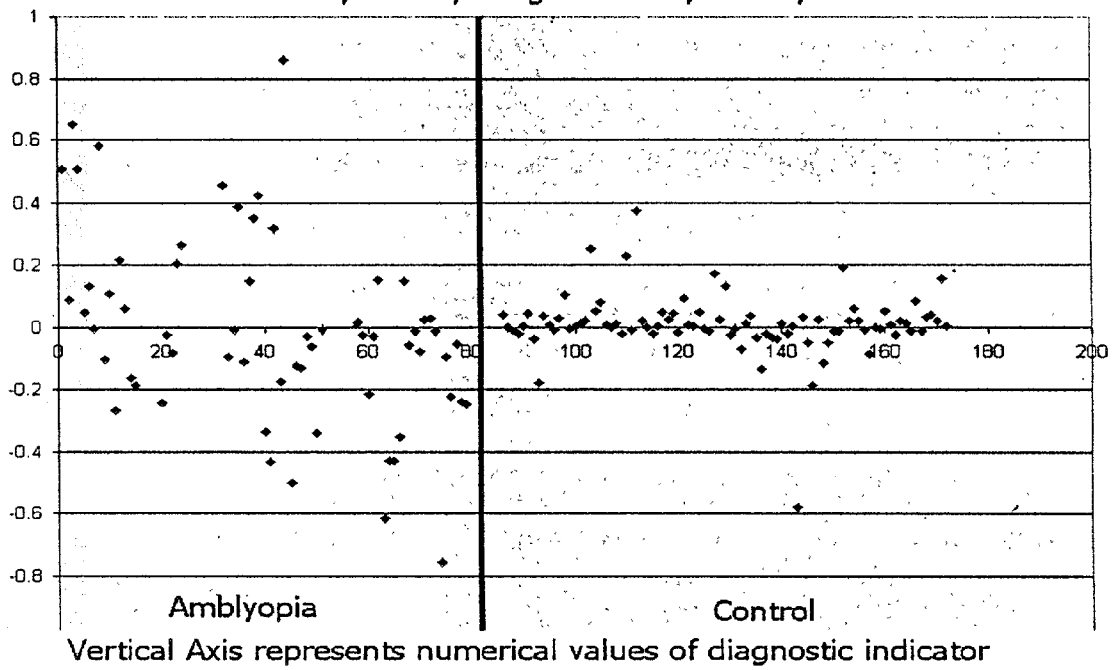
FIG. 5 is a graph of numerical values of a diagnostic indicator of the present invention demonstrating differences between normal eyes and amblyopic eyes.

One way of correlating disorders of the eye with particular ones of the algorithms is to simply compare the results from the algorithm with results of a conventional clinical examination. After a number of such comparisons, the algorithms predictive of a disorder become apparent empirically. Another statistical method of determining significance of an algorithm in predicting Amblyopia may be done by Multiple Regression Analysis or other similar statistical tools of the individual algorithmic values obtained from two predefined clinical groups of persons. One group(s) includes persons with Amblyopia and/or other diseases, and the other group is a control group known to possess clinically normal eyes. Yet another method of correlating disorders of the eye with particular ones of the algorithms utilizes the AutoFilter and Advance Filter capabilities found in MICROSOFT OFFICE™. In an example using this technique, the Control Group and the Amblyopia Group were arranged such that the individual algorithmic values are compared in a plot chart as shown in FIG. 5. Here, the values to the left of the dark vertical bar are the amblyopic group values produced by this particular algorithm (Left intra-symmetry—right intra-symmerty) and the values to the right are from the Control Group. It is evident that many of the values in the amblyopic group are different, either greater or lesser, than the values found in the control group.

Then by utilizing the Filter programs (in MICROSOFT OFFICE™), the most appropriate value to separate the two groups may be determined. In this manner, a list of algorithms were obtained that are associated with either bilateral balance, refraction, or alignment.

A particular value derived from a particular algorithm is specific for a particular disease state in only a small percentage of cases. Combining algorimithic values together in sub-groups of algorthms that demonstrate a degree of high correlation with a particular disease state improves percentage of correct correlation of the algorithmic values to the underlying clinical condition and the identification of a specific disease process.

These sub-grouping of algorithmic values take on geometric shapes (profiles) when arranged together, and those configurations are of the generic ocular condition represented (see previous graphic description of Wavefront Analysis of Normal) by the particular disease or ocular state, such as Amblyopia or Normal. As will be described, perhaps one of the best ways to make these configurations apparent is the "Radar" plot and/or Bubble Graphs, although other presentations of the configurations may also be feasible.

The following 21 algorithms, which are described in detail and given by way of example of one technique of the present invention, are related to bilateral balance and were found to be associated with amblyopic persons. Other algorithms additionally listed in Appendix A demonstrate that there are potentially many algorithmic determinations of disease states that possibly may be used as well. Some of these algorithms are found more predictive than others to a particular state. These algorithms were isolated using Microsoft Office Excel™ and Minicab Statistical Software™.

EYE BALANCE UNCOMPENSATED—Maximum value of the cross correlation of the left pupil intensity image within left/right horizontally flipped right pupil intensity image.

EYE BALANCE CROPPED—the maximum value of the cross correlation of the left pupil intensity image with the left/right flipped right pupil intensity image for each pupil image has been normalized by its respective cumulative energy. The energy for each pupil is calculated by summing the intensity values of each pixel inside the pupil disk. This has the effect of removing the absolute magnitude as a distinguishing factor between the left and right pupil, thereby permitting a more restricted comparison between the shapes of the intensity distribution in the two pupils.

EYE BALANCED NORMED & CROPPED—the maximum value of the cross correlation of the left pupil intensity image within left/right flipped, right pupil intensity image where each pupil image has been normalized and cropped identically as described above. This has the effect of removing from consideration minimum distortions in the shapes between the two eyes and the absolute magnitudes between the two eyes, thereby leaving only the relative differences in the shape of the intensity distribution as a distinguishing characteristic.

RIGHT PUPIL/LEFT PUPIL SPIKE PATCH MEDIAN—Ratio of the right/left of the median of the intensity of the pixels of a 13×13 pixel square patch around the corneal specular reflex.

RIGHT PUPIL/LEFT PUPIL MEANS—Ratio of the right/left average of all the pixel values of the pupillary disk.

RIGHT PUPIL/LEFT PUPIL STD—Ratio of the right/left standard deviation of all the intensity levels of all the pixels in the pupillary disk.

RIGHT PUPIL/LEFT PUPIL SKEWNESS—This is a ratio of the right pupil/left pupil skewness of all the intensity levels of all pixels in the pupillary disk.

RIGHT PUPIL/LEFT PUPIL PEAKEDNESS—Ratio of the right/left data peakedness of all the intensity levels in the pupillary disk.

RIGHT PUPIL/LEFT PUPIL TOP ROWLINSCOPE—Ratio of the right/left topography row linear slope, which is the slope parameter for the linear curve fit to the median values of the intensity of light in the rows of the pupil disk.

RIGHT PUPIL/LEFT PUPIL ROWLININTERCEPT—Ratio of the right/left topography rows linear intercept which is the intercept parameter for a linear curve fit to the median values in the rows of the pupil disk pixels.

RIGHT PUPIL/LEFT PUPIL ROWQUADQUAD—Ratio of the right/left topography rows quadratic quartic which is the quadratic parameter for the quadratic curve fit to the mean intensity values of the pupillary disk.

RIGHT PUPIL/LEFT PUPIL TOP COLSQUADQUAD—Ratio of the right/left topographic columns quadratic quartic, which is the quadratic parameter for the quadratic curve fit to the median intensity values of the columns of the pupillary disk.

RIGHT PUPIL/LEFT PUPIL HIRSRAD MM—Ratio of the right/left Hirshberg radius MM, which is the radius distance in millimeters from the geometric center of the pupillary disk to the center of the corneal specular reflex.

RIGHT PUPIL/LEFT PUPIL HIRSTOTDEV AXIS—Ratio of the right/left Hirshberg total deviation axis, which is the ratio of the angles of the axis formed by the radius from the geometric center of the pupil disk to the center of the corneal specular reflex reflection in degrees.

RIGHT PUPIL/LEFT PUPIL HIRSTOT DEVIATION—Ratio of the right/left total Hirshberg deviation, which is the absolute magnitude of the deviation of the corneal specular reflex from the geometric center of the pupil independent of its direction of deviation. It represents the distance in "angle vector space" from the center of the pupil disk to the corneal specular reflex.

RIGHT PUPIL/LEFT PUPIL HIRSNASAL DEVIATION—Ratio of the right/left Hirshberg nasal deviation, which is the horizontal angle from the axis through the center of the pupil disk to the axis through the corneal specular reflex reflection in degrees.

RIGHT PUPIL/LEFT PUPIL VERTICAL DEVIATION—Ratio of the right/left Hirshberg vertical deviation, which is the vertical angle space measurement from the axis through the center of the pupil disk to the axis through the corneal specular reflex reflection in degrees.

RIGHT PUPIL/LEFT PUPIL INTRASYMMETRY—Ratio of the right/left intrasymmetry, which is the symmetry of the pupil with itself within the pupillary disk.

INTERSYMMETRY—A two-dimensional correlation coefficient between the left pupil image and a duplicate of the right pupil image which has been flipped along the left/right vertical axis, thereby quantifying the comparative global symmetry of the two pupil image intensity distributions Likewise, profile sub-groupings of algorithms have been found that correlate to astigmatism, binocular balance, refractive errors, alignment and reading disorders. Accordingly, listed below are tables containing algorithms specific to alignment, refraction, and the aforementioned bilateral balance ratio. As with the other algorithms, a more detailed description of the algorithm so as to be understandable to one skilled in the art is found in Appendix A.

Bilateral Balance Ratio

R/LPSpikePatchEdgeMedian
RP/LPSpikePatchEdgeStd
RP/LPMean
RP/LPMedian
RP/LPStd
RP/LPSkewness
RP/LPPeakedness
RP/LPRadMeanHarm
RP/LPMoment.N20
RP/LPMoment.N21
RP/LPMoment.Hu4
RP/LPTopography.Rows.Linear.Intercept
RP a network of the originated that was/LPTopography.Rows.Linear.Slope
RP/LPTopography.Rows.Quad.Intercept
RP/LPTopography.Rows.Quad.Slope
RP/LPTopography.Rows.Quad.Quartic
RP/LPTopography.Cols.Linear.Intercept
RP/LPTopography.Cols.Linear.Slope
RP/LPTopography.Cols.Quad.Intercept
RP/LPTopography.Cols.Quad.Slope RP/LPTopography.Cois.Quad.Quartic
RP/LPHirschberg.RadiusMM
RP/LPHirschberg.TotalDeviationAxis
RP/LPHirschberg.TotalDeviation
RP/LPHirschberg.NasalDeviation
RP/LPHirschberg.VerticalDeviation RP/LPIntraSymmetry Amblyopic Factors LPSpikePatchEdgeStd
LPMean
LPMedian
LPStd
LPSkewness
LPPeakedness
LPRadMeanHarm
LPMoment.N20
LPMoment.N21
LPMoment.Hu4
LPTopography.Rows.Linear.Intercept
LPTopography.Rows.Linear.Slope
LPTopography.Rows.Quad.Intercept
LPTopography.Rows.Linear.Slope
LPTopography.Rows.Quad.Intercept
LPTopography.Rows.Quad.Slope
LPTopography.Rows.Quad.Quartic
LPTopography.Cols.Linear.Intercept
LPTopography.Cols.Linear.Slope
LPTopography.Cols.Quad.Intercept
LPTopography.Cols.Quad.Slope
LPTopography.Cols.Quad.Quartic
LPHirschberg.RadiusMM
LPHirschberg.TotalDeviationAxis
LPHirschberg.TotalDeviation
LPHirschberg.NasalDeviation
LPHirschberg.VerticalDeviation
LPIntraSymmetry
RPIntraSymmetry
RPHirschberg.VerticalDeviation
RPHirschberg.NasalDeviation
RPHirschberg.TotalDeviation
RPHirschberg.TotalDeviationAxis
RPHirschberg.RadiusMM
RPTopography.Cols.Quad.Quartic
RPTopography.Cols.Quad.Slope
RPTopography.Cols.Quad.Intercept
RPTopography.Cols.Linear.Slope
RPTopography.Cols.Linear.Intercept
RPTopography.Rows.Quad.Quartic
RPTopography.Rows.Quad.Slope
RPTopography.Rows.Quad.Intercept
RPTopography.Rows.Linear.Slope
RPTopography.Rows.Quad.Intercept
RPTopography.Rows.Linear.Slope
RPTopography.Rows.Linear.Intercept
RPMoment.Hu4
RPMoment.N21
RPMoment.N20
RPRadMeanHarm
RPPeakedness
RPSkewness
RPStd
RPMedian
RPMean
RPSpikePatchEdgeStd Refraction Factors LPTopography.Cols.Quad.Quartic
LPTopography.Cols.Quad.Slope
LPTopography.Cols.Quad.Intercept
LPTopography.Cols.Linear.Slope
LPTopography.Cols.Linear.Intercept
LPTopography.Rows.Quad.Quartic
LPTopography.Rows.Quad.Slope
LPTopography.Rows.Quad.Intercept
LPTopography.Rows.Linear.Slope
LPTopography.Rows.Linear.Intercept
LPMoment.Hu4
LPMoment.N21
RPMoment.N21
RPMoment.Hu4
RPTopography.Rows.Linear.Intercept
RPTopography.Rows.Linear.Slope
RPTopography.Rows.Quad.Intercept
RPTopography.Rows.Quad.Slope
RPTopography.Rows.Quad.Quartic
RPTopography.Cols.Linear.Intercept
RPTopography.Cols.Linear.Slope
RPTopography.Cols.Quad.Intercept
RPTopography.Cols.Quad.Slope
RPTopography.Cols.Quad.Quartic Alignment factors LPStd
LPMedian
LPMean
LPSpikePatchEdgeStd
LPHirschberg.RadiusMM
LPHirschberg.TotalDeviationAxis
LPHirschberg.TotalDeviation
LPHirschberg.NasalDeviation
LPHirschberg.VerticalDeviation
LPIntraSymmetry
RPIntraSymmetry
RPHirschberg.VerticalDeviation
RPHirschberg.NasalDeviation
RPHirschberg.TotalDeviation
RPHirschberg.TotalDeviationAxis
RPHirschberg.RadiusMM
RPSpikePatchEdgeStd
RPMean
RPMedian
RPStd Once the wavefront information is obtained and the above relationships calculated, the results may be presented as either a string of numbers that can be manipulated in the Advanced Filter and Auto Filter of the EXCEL™ Program to make a determination of the disease process. Additionally, those same values may be presented in any of several graphic formats for ease of visual, clinical interpretation.

Figure 6:
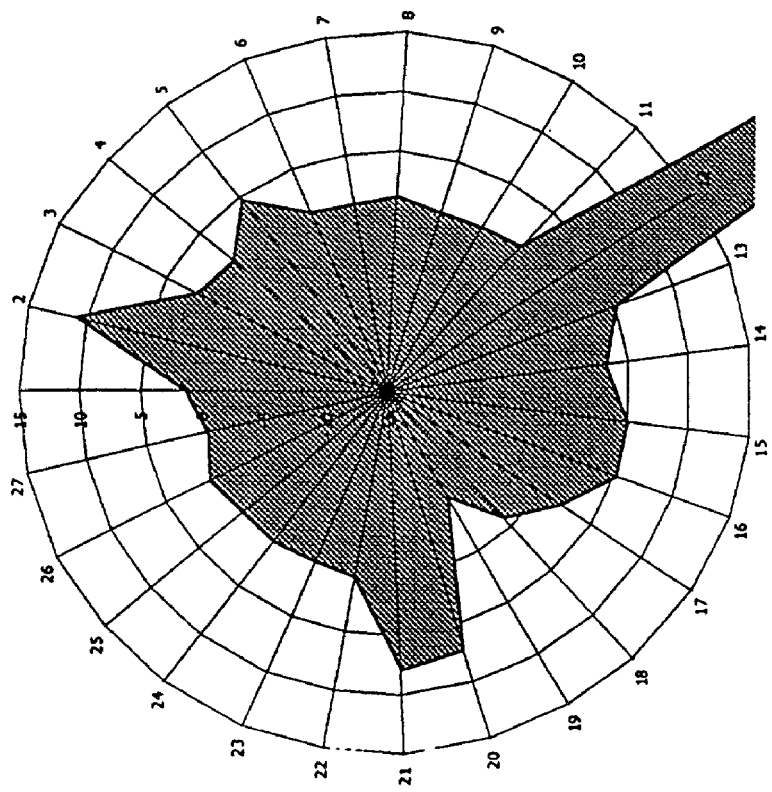

One such presentation format, as shown in FIGS. 1a–1d, which by way of example and as described above shows a graph of bilateral balance ratio, Amblyopic factors, Refractive factors and Alignment factors of the individuals with normal eyes, may be generated using MICROSOFT™ EXCEL™. This is a radar circular presentation wherein each indicated radius value is representative of an algorithmic scale, with a center of the diagram representative of a negative number, with concentric, generally circular indices representative of positive going graduations extending as shown outwardly from the center. These radially extending graduations may be set to any scale desired or necessary to fully illustrate any diseases or disorders an individual may have. In one embodiment of the present invention, the scale is selected generally in accordance with a maximum abnormal value of any of the algorithm values for that test. A default scale may be used in the instance where there are no extreme abnormal values, i.e. where an eye is relatively normal. The particular measurement or statistical calculation made is represented by a radially extending line, with data points on these lines being connected, the envelope thereby formed being filled with a readily identifiable marking or structure, such as shading, hatching or a color. In order to make any disease or disorder that a subject be afflicted by stand out more prominently in the presentation, statistical measurements and calculations relating to a particular disease or disorder may be grouped together.

Where the algorithms indicate a bilateral balance ratio wherein algorithm values of one eye are compared to algorithm values of the other eye, and referring again to FIG. 1a, it will be noted that the results of the selected algorithms for bilateral balance are generally close to 1 (unity), indicating a normal eye. These algorithms all measure a ratio of the right pupil with respect to the left pupil, although a ratio of the left eye with respect to the right eye should be equally significant. In contrast, and referring to FIG. 6, a bilateral balance ratio is shown of a subject wherein algorithm values from the subject's eyes are not balanced or generally equivalent, and thus this subject has problems that are indicated by a ratio of algorithm values that deviate significantly from zero, radically altering the shape of the graph from that shown in FIG. 1a. As shown in FIG. 6, the ratios for the algorithm RP/LP topographyrowsquadquartic and RP/LP topographyrowsquadslope are very unbalanced, indicating a significant difference between the eyes. Referring to appendix A, it is seen that these algorithms are the quadratic parameter for a quadratic curve fit to the median of the columns of the pupil disk pixels and the slope parameter of a quadratic curve fit to the median of rows of pupil disk pixels, respectively. Such a bilateral balance ratio algorithm is useful as a diagnostic indicator of binocularity. This algorithm determines to what extent optical characteristics (i.e., the object of regard, it's focus and size) of an image created by an individual's eyes are balanced, and by direct inference, the degree of similarity and ease of visual integration of the right and left images into a single perception.

Figure 1C:
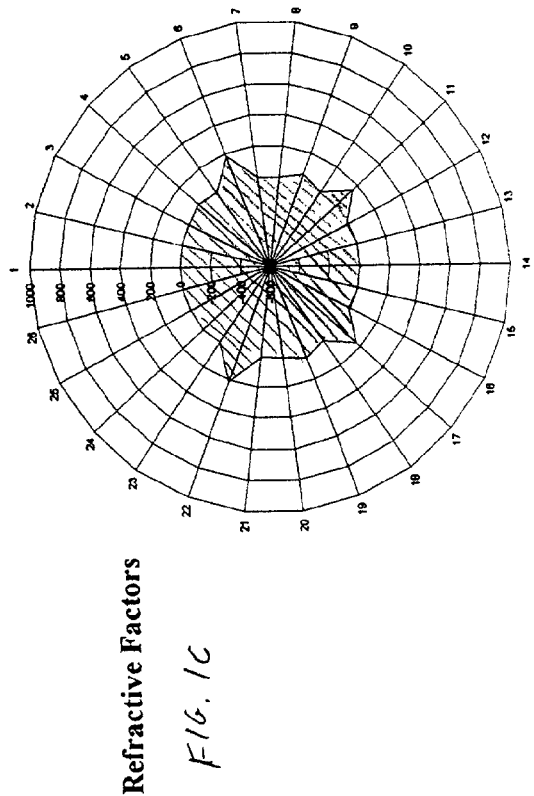
FIG. 1c illustrates median values of a control group of individuals having relatively normal eyes, in plot form, of refractive factors.
Figure 7:
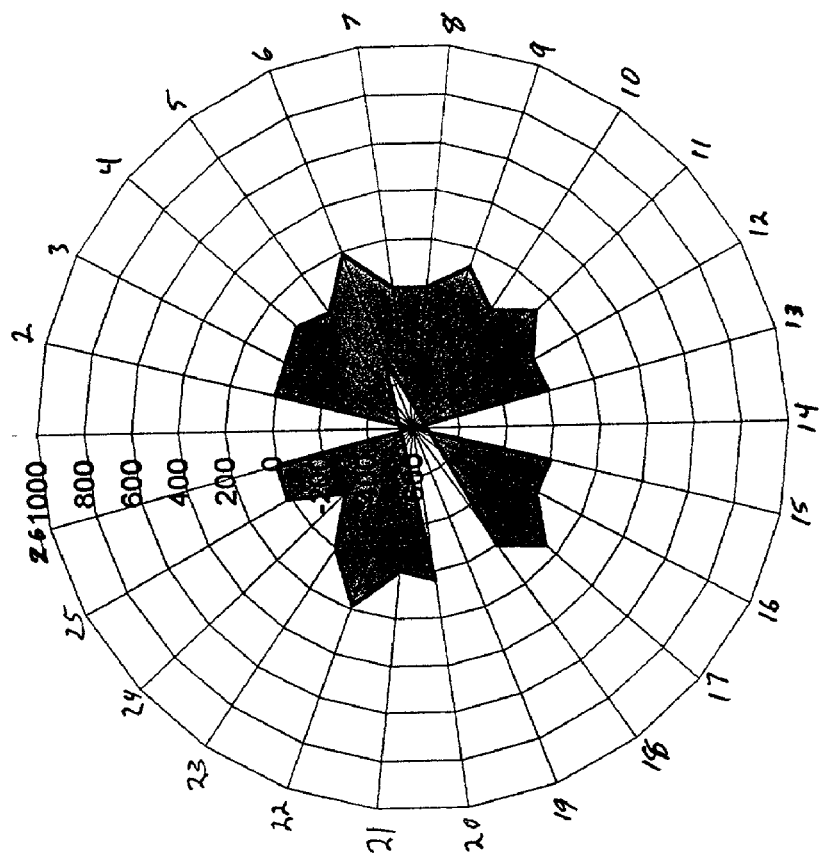
FIG. 7 is a graphical presentation as shown in FIG. 6 wherein refraction between the two eyes is different as contrasted to FIG. 1c.

In the instance where a test of refraction is performed, and referring to FIG. 1c, one possible arrangement of the algorithms in a graphical format as described produces a symmetrical form. This form, in the normal eye as shown, generally resembles opposed butterfly wings. Here, the values of the algorithms from a normal pair of eyes are again relatively close to zero, with any excursions from zero being symmetrical due to the same algorithms for each eye positioned opposite one another in horizontal relation. The open gaps at the top and bottom of the "wings" are zero values along a vertical median. In contrast, FIG. 7 is a graph indicating a problem of refraction of an individual in which both eyes are nearsighted. In addition, asymmetry of the graphs further indicate an imbalance between the eyes of each individual.

Figure 8:
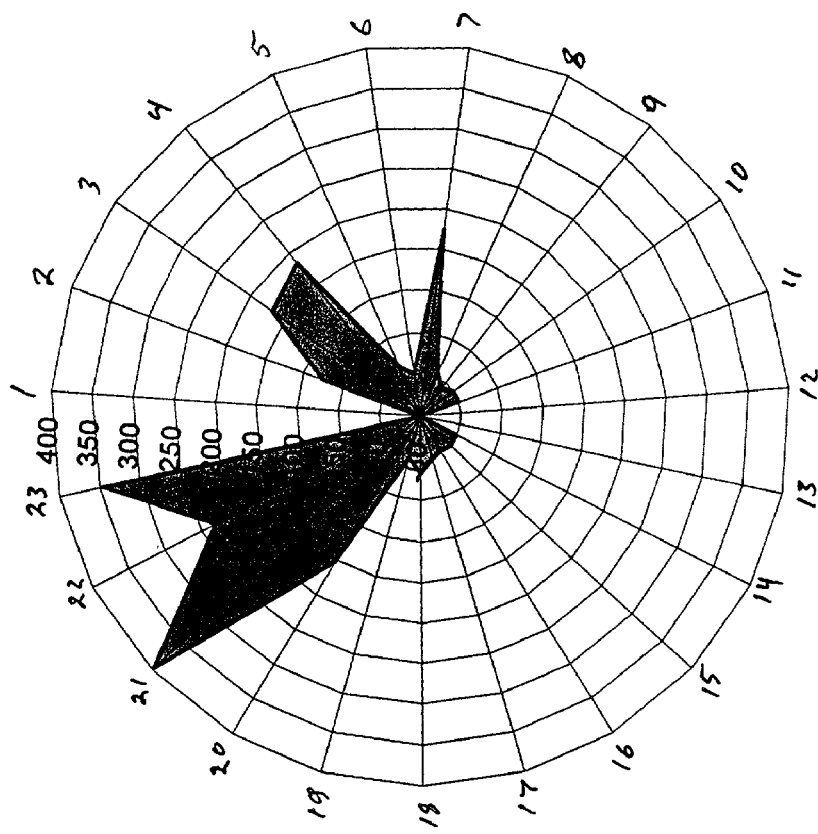
FIG. 8 is a graphical presentation as described for FIG. 1d wherein there are differences of alignment between the two eyes.

FIG. 1d, as stated, shows a graph of a median of alignment factors from the control group of eyes. In this graph, while some asymmetry exists, the scale is such that differences of alignment between the eyes is relatively small. In contrast, FIG. 8 shows greater, more significant differences between the eyes.

Figure 9:
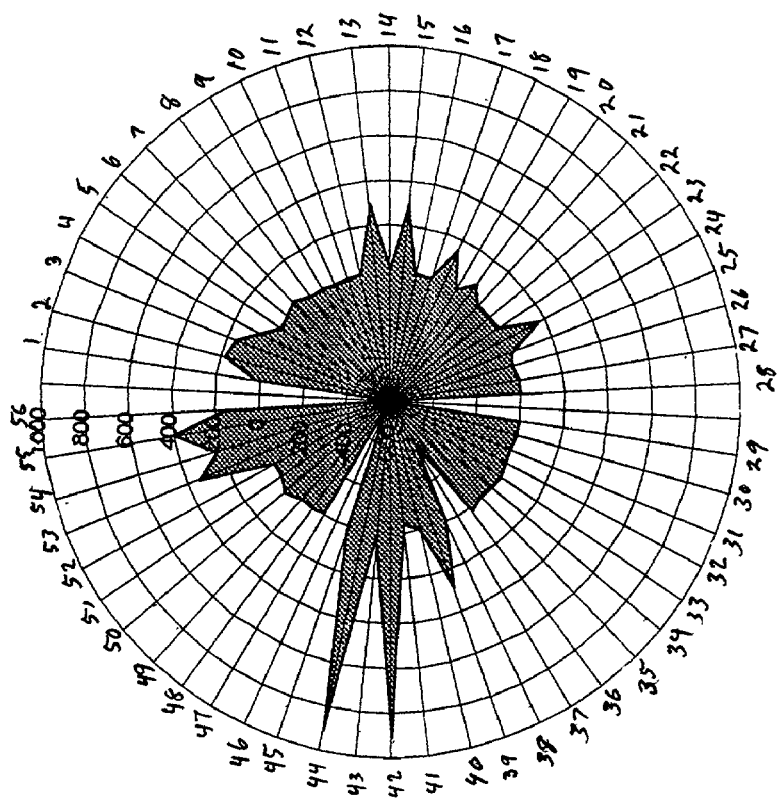
FIG. 9 is a graphical presentation of the algorithms shown in FIG. 1b illustrating Amblyopia.

As stated above, the factors related to alignment and refraction may be combined, and may be used with other algorithms to indicate Amblyopia, the absence of which being shown in FIG. 1b. As described above, symmetry between the right and left graphs indicates a nearly perfect eye. This is in contrast to FIG. 9 where asymmetry of the graphs indicates different results for refraction and alignment from the respective, same algorithm for each eye.

Figure 10:
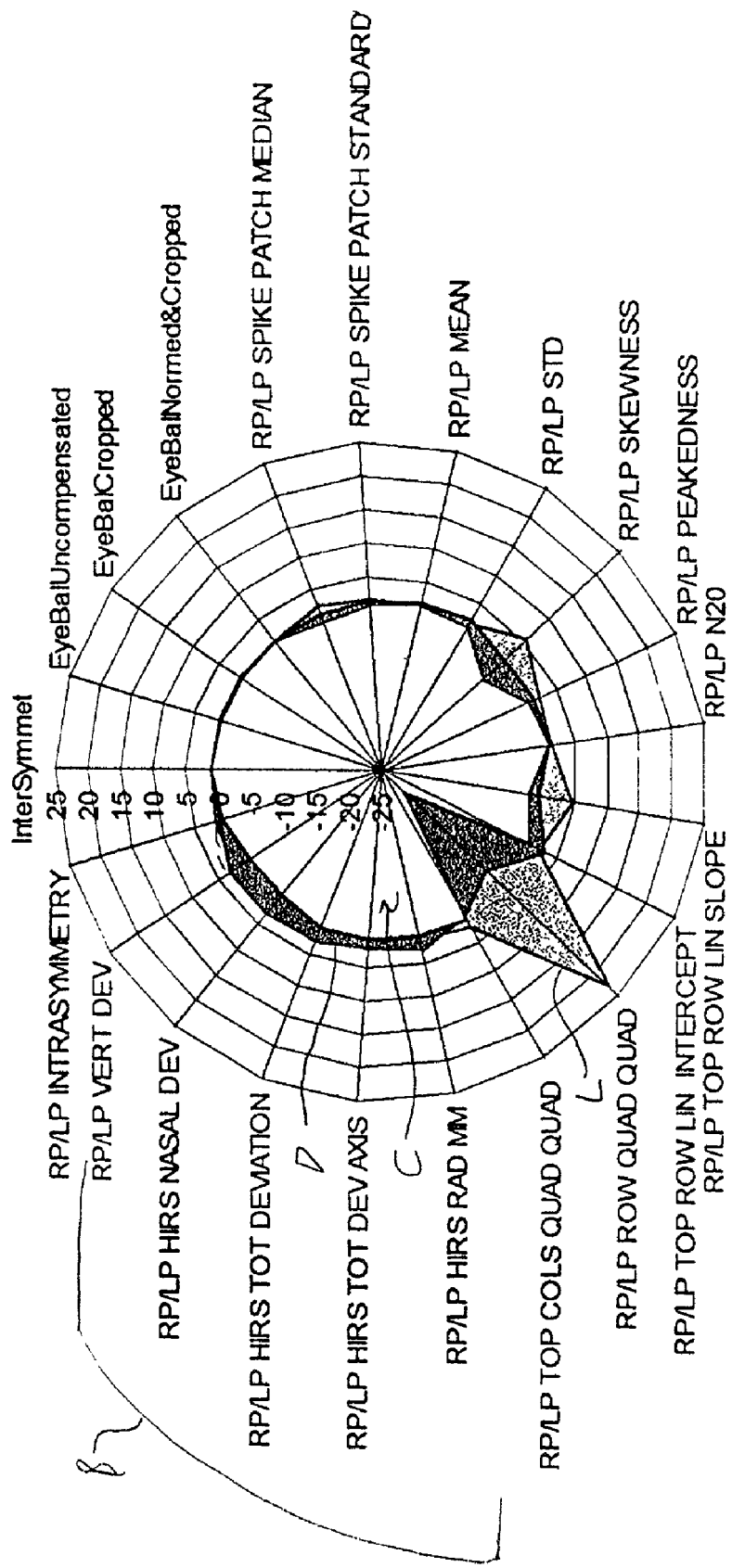
FIG. 10 is a graphical presentation of eye balance using algorithms selected to compare eyes under test with minimum and maximum values for normal eyes.

In another presentation format as shown in FIG. 10, the results of the algorithms for the bilateral balance ratio of two eyes from a subject are compared to a bilateral balance ratio representative of a pair of normal eyes, as statistically determined by a relatively large database of individuals whose eyes have been clinically determined to be normal. As such, a plurality of measurements or calculations are taken from eyes of the subject under test, and compared to the same measurements and calculations, plus or minus one standard deviation, taken from the clinically-determined grouping of matched individuals possessing normal eyes. This is shown in FIG. 10, where the lightly-shaded outline or envelope L is normal data plus one standard deviation and the clear outline or envelope C is normal data minus one standard deviation. The data from the subject under test is the darkly-shaded outline or envelope D. With this type of presentation, data from a subject with normal eyes forms an envelope between the envelopes defined by the plus and minus one standard deviation of data from a normal eye, as shown in FIG. 10. With this presentation, any significant excursions of the subject's eye data outside either of the normal envelopes is readily apparent. For example, FIG. 10 shows an individual with alignment problems, as indicated by deviation of the Hirshberg algorithms outside the range of +1 standard deviation. Such problems may be pronounced in graphic form by grouping them together, as indicated by bracket B showing how all the Hirshberg algorithms, which are related to alignment, are grouped.

Figure 11:
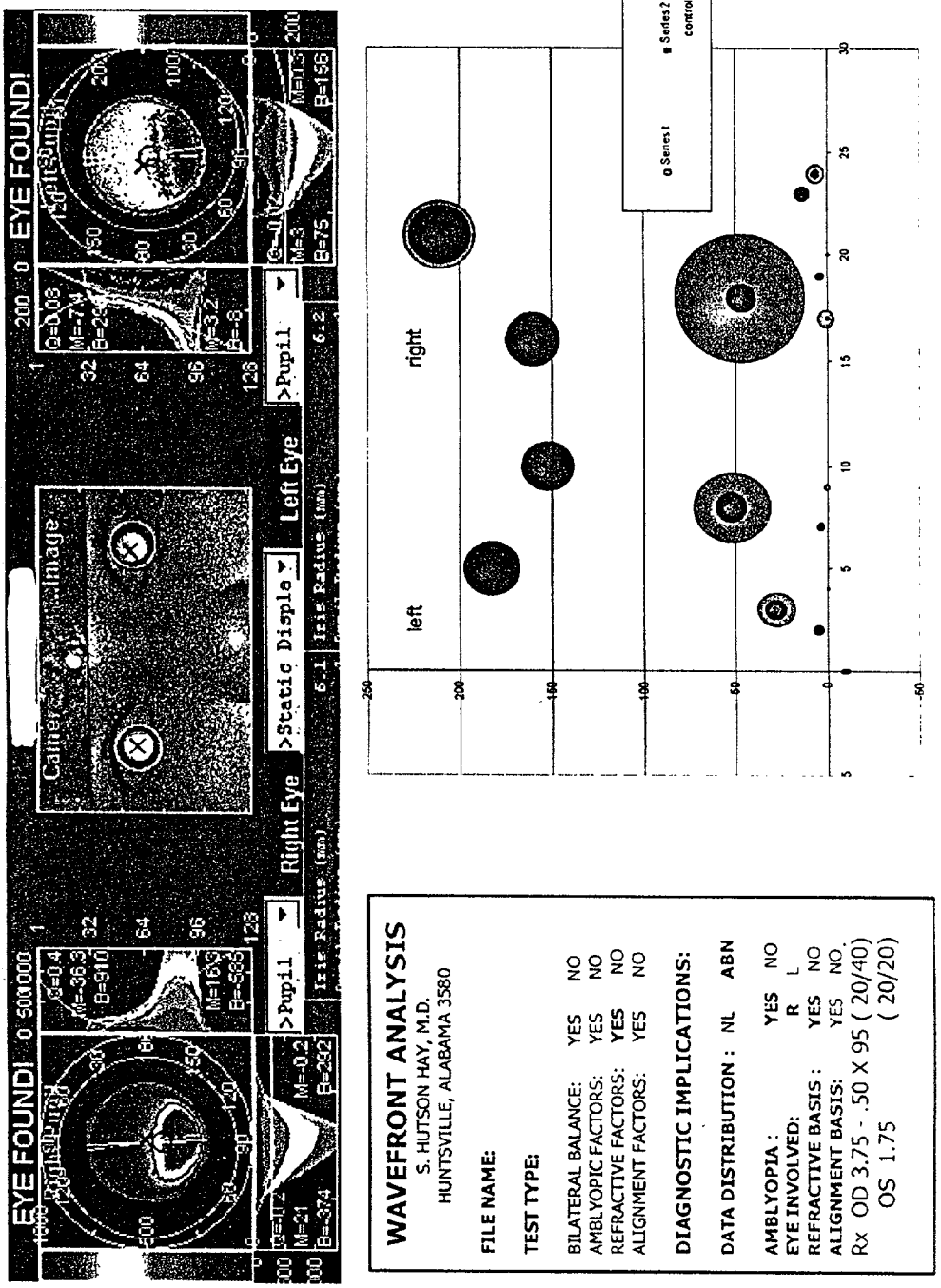
FIG. 11 illustrates how a bubble graph may be used to display data of the present invention, along with a display including other information.

While the above presentation formats are believed to be most useful, other presentation formats may be used as shown in FIG. 11, which shows a "bubble graph" format. The "Bubble Graph" format is very useful to present complex clinical information contained in this type of a multiple valued determination. In this format, "X" and "Y" axes of the graph are set to a "standard" set of known values of a known clinical condition, most commonly for a Control group ("NORMAL") of values, but which could be set for some other known sub-grouping of values, for example those of a particular type of Amblyopia. The set standard is selected based on information desired to be learned by analysis of an unknown eye image. If for example, it is desired to see how close unknown eye data is to a known "Normal" condition, then the standard is selected for those values obtained from the Control Group's median of normal values. In attempting to determine Amblyopia or Strabismus, a similar situation would exist but the set standard would be that particular type of Amblyopia or Strabismus under consideration.

The Bubble Graph then presents the data color-coded or otherwise identified such that the standard data is plotted in a different color or with different markings than the unknown eye data. The value size and placement of each bubble is then representative of a particular algorithmic value. It becomes a simple visual task to match the distribution of data between those values that are clinically known values and those values found in the individual unknown clinical state.

In addition to the foregoing, any of the graphical presentations as described above may include a format that shown in FIG. 11. An upper central region may include an image of eyes of the subject as obtained by the reflex photometer. Indications may be included showing that the eyes are located, such as the circles surrounding the irises of the eyes. Additional Indica may be provided, such as the X-marks showing location of the specular reflection from the cornea. Here, it is readily seen that the left eye in this instance is in-turning as the specular reflection is not centered within the circle indicating diameter of the iris. To the right the left of the central display are boxes indicating detailed data with respect to each eye, such data including colorization, topography, quadratic and linear fits and an indication that the eye was located. To the left central area of the display is located a box containing data related to the subject's name, the type of test performed, and diagnostic implications.

In yet another embodiment of the invention, a centralized location may contain analysis files and a database containing results of a relatively large number of analyses from individuals. Users such as clinicians, ophthalmologists, screening organizations, and others may subscribe to a service wherein an image of eyes of a subject under test are sent telephonically, such as over the Internet or by other communications mediums such as a wireless system, from a remote location to the central location. The image would be analyzed at the central location and a graph in a format such as one of those described above sent back to the subscriber. Such a system would be advantageous inasmuch as clusters of eye diseases, which may be related to harmful environmental factors or other factors, may be readily identified. In addition, the database would continually grow and provide a large database for archival purposes and for future study.

In any of the described embodiments, it should be apparent that a plurality of images of eyes of a subject may be taken over a period of time to track changes in the subject's eyes. This is particularly useful when following progression of a disease or eye disorder(s), either binocular or monocular, such as seen in the development of cataracts. In addition, tracking changes of a condition following ophthalmic or medical treatment, such as post operative evaluation of LASIK surgery, or treatment of Amblyopia or Refractive Errors may be accomplished.

Having thus disclosed my invention and the manner of its use, it should be apparent to one skilled in the art that incidental modifications may be made thereto that fairly fall within the scope of the following appended claims, wherein

I claim:

1. A method for determining optical status of each individual eye of a pair of eyes of a subject comprising the steps of:
   A) imaging both of said pair of eyes using a digital imaging device while utilizing a standard set of uniform imaging conditions and visual tasks while performing said imaging,
   B) isolating a retinal reflex from each of said pair of eyes,
   C) applying a series of algorithms to statistically determine a plurality of parameters related to each said retinal reflex, and
   D) establishing validity of a subsequent analysis of image data by determining the monocular state of fixation of each of said pair of eyes.

2. A method as set forth in claim 1 further comprising the step of reducing the image data to a common clinical state, whereby valid mathematical manipulation of image data either as individual or composite group measurements is permitted.

3. A method as set forth in claim 2 further comprising the step of collecting all data from a plurality of subjects in the same manner and utilizing a reproducible visual task, and achieving and confirming that each said subject's gaze is in "Optimal Visual Perception".

4. A method as set forth in claim 1 further comprising the step of comparing said plurality of parameters from each said retinal reflex taken from said individual to a like set of parameters taken from a normal retinal reflex.

5. A method as set forth in claim 4 further comprising the steps presenting said plurality of parameters from one of said retinal reflexes taken from said individual and said parameters from the other of said retinal reflexes taken from said individual in a circular graphical format, with said parameters from one of said retinal reflexes arranged on one side of said circular graphical format and said parameters from the other of said retinal reflexes arranged symmetrically on the other side of said circular graphical format.

6. A method as set forth in claim 1 further comprising the step of comparing said plurality of parameters from each said retinal reflex taken from said individual to a like set of parameters taken from a normal eye.

7. A method as set forth in claim 6 further comprising the step of calculating a range of said parameters taken from a normal retinal reflex and superimposing said plurality of parameters from one of said retinal reflexes taken from said individual over said range of said parameters taken from said normal retinal reflex.

8. A method as set forth in claim 1 further comprising the step of comparing said plurality of parameters from one of said retinal reflexes taken from said individual with parameters from the other of said retinal reflexes taken from said individual.

9. A method as set forth in claim 1 further comprising the step of presenting said plurality of parameters from one of said retinal reflexes taken from said individual and said parameters taken from a normal retinal reflex in a circular graphical format.

10. A method as set forth in claim 6 further comprising the step of superimposing said plurality of parameters from one of said retinal reflexes taken from said individual over said parameters taken from a normal retinal reflex.

11. A method as set forth in claim 1 further comprising the step of selecting said algorithms based on their predictivity of eye disorders.

12. A method as set forth in claim 1 further comprising the step of selecting said algorithms based on their predictivity of ocular balance between said retinal reflexes.

13. A method for determining disorders of eyes of a subject comprising the steps of:
   A) obtaining a retinal reflex in digital format from each of said eyes,
   B) for each eye disorder of said disorders of eyes, performing statistical calculations using a plurality of statistical algorithms on each said retinal reflex, said statistical calculations performed on selected areas of each said retinal reflex,
   C) comparing results of said statistical calculations taken from one said retinal reflex with results from the same statistical calculations taken from the other said retinal reflex,
   D) plotting results from C) so that certain eye disorders that may be present in said subject are evident in said plot, and
   E) plotting said results in a circular plot, with said statistical calculations taken from one said retinal reflex arranged along one side of said circular plot and said statistical calculations taken from the other said retinal reflex positioned on the other side of said circular plot, with identical statistical calculations from each said retinal reflex being in opposed relation.

14. A method for statistically determining a plurality of values of generic disease groups, and comprising the steps of:
  A) obtaining photometric imaging readings using digital imaging device of wavefront ocular images using uniform imaging circumstances for each of said wavefront ocular images, said wavefront ocular images taken from persons with clinically known disease processes,
  B) grouping persons with similar disease processes or associated ocular states together in clinical subgroups,
  C) summing values of those identical algorithms found in said clinical sub-groups to obtain statistical measurements and then performing a statistical analysis on said statistical measurements to obtain statistical data, and
  D) utilizing said statistical data to define features in graphic format that characterizes values of the subgroup with a particular disease.

* * * * *